(12) United States Patent
Cormier

(10) Patent No.: US 6,855,300 B2
(45) Date of Patent: Feb. 15, 2005

(54) SOLUTE DISPERSION DEVICE

(75) Inventor: David G. Cormier, Scottsdale, AZ (US)

(73) Assignee: Great American Duck Races, Inc., Scottsdale, AZ (US)

( * ) Notice: Subject to any disclaimer, the term of this patent is extended or adjusted under 35 U.S.C. 154(b) by 84 days.

(21) Appl. No.: 10/383,456

(22) Filed: Mar. 6, 2003

(65) Prior Publication Data

US 2004/0175311 A1 Sep. 9, 2004

(51) Int. Cl.$^7$ ................................. B01D 11/02
(52) U.S. Cl. .................... 422/265; 422/261; 422/264; 441/23; 441/24
(58) Field of Search ................. 422/265, 261, 422/264; 441/23, 24

(56) References Cited

U.S. PATENT DOCUMENTS

| | | | | |
|---|---|---|---|---|
| 3,598,536 A | * | 8/1971 | Christensen | 422/264 |
| 3,607,103 A | | 9/1971 | Kiefer | |
| D242,705 S | | 12/1976 | Fedrigo | D23/3 |
| 4,067,808 A | | 1/1978 | Phillips | 210/169 |
| 4,202,858 A | | 5/1980 | Bruce et al. | |
| 4,241,025 A | | 12/1980 | Grayson, IV et al. | 422/263 |
| 4,419,233 A | | 12/1983 | Baker | 210/169 |
| 4,473,533 A | * | 9/1984 | Davey | 422/265 |
| D286,560 S | * | 11/1986 | Wolfe | D23/207 |
| 4,630,634 A | | 12/1986 | Sasaki et al. | 137/268 |
| 4,691,732 A | | 9/1987 | Johnson et al. | 137/268 |
| 4,798,707 A | * | 1/1989 | Thomas et al. | 422/264 |
| 4,828,804 A | * | 5/1989 | Nicholson et al. | 422/264 |
| 4,997,540 A | | 3/1991 | Howlett | 204/271 |
| 5,059,316 A | | 10/1991 | Renton | |
| 5,225,074 A | | 7/1993 | Moini | 210/169 |
| 5,441,711 A | | 8/1995 | Drewery | 422/264 |
| 5,476,116 A | | 12/1995 | Price et al. | 137/268 |
| 5,662,795 A | | 9/1997 | Pickens et al. | |
| 5,795,551 A | | 8/1998 | Powell | |
| 5,888,386 A | | 3/1999 | Enright et al. | 210/169 |
| 6,123,842 A | | 9/2000 | Buchan | |
| 6,221,244 B1 | | 4/2001 | Yassin | 210/169 |
| 6,238,553 B1 | | 5/2001 | Lin | |
| 6,253,950 B1 | | 7/2001 | Buck et al. | |
| 6,340,431 B2 | | 1/2002 | Khan | |
| 6,432,371 B1 | | 8/2002 | Oliver, Jr. | |
| 2002/0078990 A1 | | 6/2002 | Munk et al. | |
| 2002/0144958 A1 | | 10/2002 | Sherman | |
| 2002/0160506 A1 | | 10/2002 | Van Erdewyk | |
| 2002/0185455 A1 | | 12/2002 | Connelly, Jr. | |
| 2003/0112012 A1 | | 6/2003 | Mosely et al. | |
| 2003/0113245 A1 | | 6/2003 | Robinson, Jr. et al. | |

OTHER PUBLICATIONS

Chlorine Dispenser (USB 63741 16827) Waterpik Technologies Canada, Inc., 240, Boulevard Industriel Boucherville, Quebec, Canada J4B 2X4 (telephone (514) 527–158), website: www.waterpik.com).

* cited by examiner

Primary Examiner—Krisanne Thornton
(74) Attorney, Agent, or Firm—Greenberg Traurig, LLP

(57) ABSTRACT

A floating device for dispersing a solute-containing solution comprised of a floatation cap in communication with a telescoping assembly having a sleeve for controlling the dispersion of the solute-containing solution is herein provided, as well as associated methods of use.

35 Claims, 7 Drawing Sheets

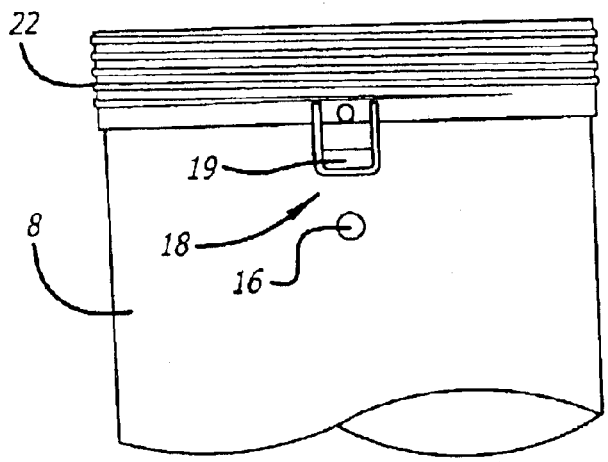
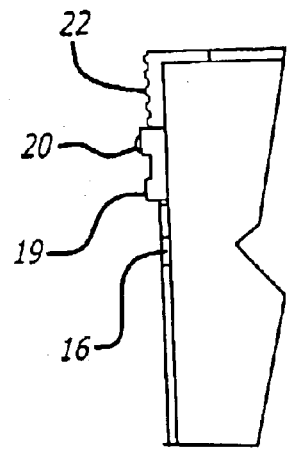
FIG. 4  FIG. 4A
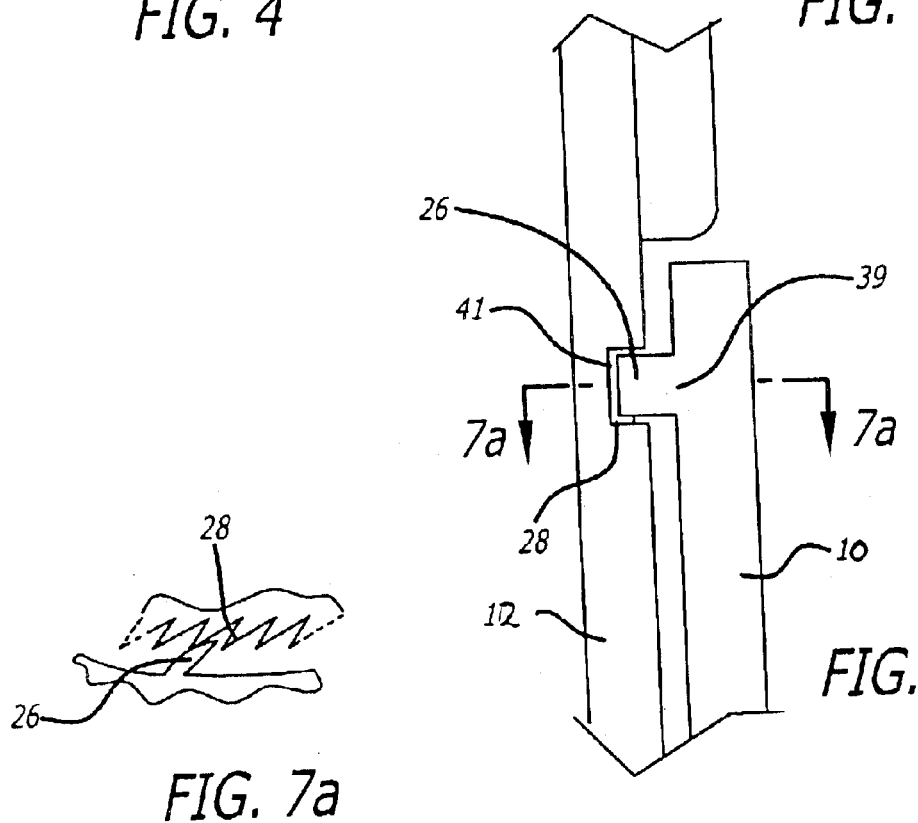
FIG. 7a  FIG. 7

SOLUTE DISPERSION DEVICE

FIELD OF THE INVENTION

This invention relates to floating solute dispersion devices. In particular, the invention is concerned with solute dispersion devices that are easy to store and transport, as well as easy to use, providing simple and clear mechanisms and methods for dispersing solute solutions at a desired rate, particularly in enclosed or partly enclosed bodies of liquid, such as pools, hot tubs and whirlpool baths.

BACKGROUND OF THE INVENTION

The dispersion of various solutes into enclosed or partly enclosed bodies of liquid is typically necessitated when such bodies are utilized as swimming/wading pools and hot tubs, for example. Unless regularly monitored and treated, the liquids, typically comprising water, can become contaminated and considered unsanitary for their intended use, such as swimming, bathing and soaking. Contamination of such bodies of water can include the growth and proliferation of algae and similar organisms to unacceptable levels. In order to contain and maintain such contamination under control so as to provide a desired sanitation level of the body of water, a regimen of controlled addition of a suitable biocide to the water is typically utilized. One example of a commonly utilized biocide is a halogen derived from a solute-bearing solution resulting from the combination of a halogen salt and water; most commonly the halogen salt is a source of chlorine. The dispensing rates of chlorine required to maintain the water in a suitable desired state depends on the size of the pool or spa, the climatic conditions, the temperature of the water, and the extent of use of the pool or spa. A floating device that can be placed in the water and accurately dispense a desired solute-containing solution into a body of water in controlled amounts eases the burden of repetitive measurement of a particular solute's concentration in a body of water and manual dispersion of such solutes as needed.

Solute dispensing devices exist for swimming pools. One such device, among many, is the Rainbow Plastics Model 330 floating dispenser for solid chlorine. This dispenser resembles an inverted hollow truncated cone. The interior serves as a receptacle into which granular pellets of water-soluble chlorine source material are placed. Around the circumference of the receptacle adjacent to the bottom are apertures consisting of elongated vertical slots. The slots cooperate with a similarly slotted sleeve which is captive to and rotatable about the exterior of the container. The sleeve can be adjusted so that the slots are fully closed, fully opened, or in between. The top of the receptacle is closable by a lid which does not make an air-tight seal with the receptacle. The walls of the container are hollow and are filled with closed-cell plastic foam. The cavity in which the foam is located is hermetically sealed. The dispenser does not incorporate any ballast elements.

When filled with a soluble solid source of chlorine or other desired halogen ion source and floated in a swimming pool, the pool water enters into the receptacle and fills it to the level at which the dispenser is floating. The water in the receptacle wets at least that source material which lies below the floating waterline of the dispenser. Accordingly, the wetted source material in the receptacle is dissolved, thereby releasing the active constituent of the material into the water in the dispenser. The rate at which such solution is released to the adjacent pool or spa is regulated by the extent to which the apertures in the receptacle are opened or closed by the position of the adjustment sleeve on the exterior of the receptacle.

Another chlorine dispensing device for dispensing a soluble solid source of chlorine i.e., for spas and hot tubs is disclosed in U.S. Pat. No. 4,630,634. Rainbow Plastics Model 335 floating dispenser conforms to the disclosure of that patent. That dispenser comprises a tubular body having a hollow pancake-shaped float at a closed upper end of the body and a tubular-shaped sleeve that fits over the opposite open end of the body. The body accommodates a predetermined volume of soluble solid halogen source material, of which a pre-selected amount is exposed to contact with the water via a plurality of elongated slots or apertures positioned at diametrically opposite locations in the sleeve, forming a solute containing solution. The body and sleeve are threadably engagable with one another to form the assembled dispensing device and are placed in the water in a vertically oriented position with the apertures immersed. The pancake-shaped float at the physical top of the body and a lead weight at the bottom of the sleeve ensures that the dispenser floats vertically erect. The rate that the solution is dispensed to the water outside the dispenser is controlled by the degree of closure of the apertures. Additionally, once the solid halogen source is completely dissolved, the latter dispenser must be reloaded by disassembling the sleeve from the body and loading the new source material into the body. The need to disassemble the dispenser when reloading can result in loss of the desired operating position adjustment of the sleeve on the body.

Other available products include cumbersome floating structures, which receive a non-refillable disposable replaceable cartridge that contains the soluble source of chlorine or other halogen. The exterior of the cartridge contains ribs which cooperate with slots in a large float to hold the cartridge in a selected position vertically relative to the float. The containers are molded with bumps axially spaced along the container adjacent to the bottom end and a single bump adjacent to the top end. The user cuts off one or more bottom bumps to define the extent to which water communicates with the inside of the container, and cuts off the top bump to provide air communication to the inside of the container. The container is then placed into the large float and the resulting assembly is placed in the pool. Water then fills the cartridge to the water line of the floating assembly; the vertical position of the cartridge in the float determines the extent to which the cartridge contents are wetted.

In a floating device for dispersing a solute-containing solution, it is important that the rate of solution of the source material be controllable with meaningful precision over a range commensurate with the solute dispersion requirements of the particular body of liquid into which it is disposed. It is therefore desirable that a floating device afford good, easy to select control over the rate at which a concentrated solute-containing solution is created within the device and over the rate at which that solution is dispensed to the exterior of the device. It is also desirable that the dispensing device not be too bulky, provide ease of storage and transport, and be aesthetically pleasing. The dispensing device should be constructed in a manner facilitating source material reloading without having to disassemble the device or disturb the adjustment for controlling the rate of solution dispensation from the interior of the device. Additionally, the device should also provide a method providing selection of the depth at which the an amount of the solute-bearing solution is dispensed to the body of liquid. Finally, the dispensing device should be made of a material, such as, but not limited to, poly vinyl chloride or acrylonitrile butadiene styrene, that are resistant to damage from prolonged exposure to sunlight and chemicals, as known in the art.

Clearly there is a need for a floating device for dispersing a solute-containing solution which is easy to store and transport, provides simple and accurate methods of use and is aesthetically pleasing.

INVENTION SUMMARY

The teachings of the invention provide a floating device for dispersing a solute-containing solution. In an exemplary embodiment, the floatation device is comprised of a floatation cap and a retractable solute-dispensing unit that is comprised of a first body in releasable communication with the floatation cap. The first body is provided with a second body in retractable communication therewith and a sleeve in sliding communication with the second body, whereby the second body and the sleeve are at least partially retractable within the first body. In a particular embodiment, junctions of various retractable components are retained in retractable communication by the use of a retaining means. One example is a locking ring at an end of the first body for retaining the second body in retractable communication with the first body.

In particular embodiments, the first body is provided with at least one aperture and the second body is further comprised of at least one aperture. Furthermore, the sleeve is also further comprised of at least one aperture. The second body may have a flanged portion at one end. In still other embodiments, the flanged portion may be further comprised of at least one protuberance for locking said second body in a protracted position.

In still other embodiments, a plurality of apertures are provided in an arrangement that results in a selected rate of dispersion of the solute-containing solution when a predetermined portion of the plurality of apertures is exposed to a body of liquid. In one exemplary embodiment, the arrangement of the plurality of apertures is provided by the second body while the sleeve's at least one aperture's position relative to the second body's plurality of apertures determines the rate of dispersion of the solute-containing solution, according to the selected positioning of the sleeve relative to the second body.

In another embodiment the configurations of the at least one aperture of the second body or the sleeve (or vise versa) are provided in a graduated arrangement such that a positioning step displays a particular aperture configuration of the graduated arrangement to the body of liquid.

In still other embodiments, the series of apertures may be provided as a series of apertures comprised of a plurality of columns and/or rows of apertures. Here, each column or row may have a differing number of apertures or be provided as sets of a plurality of apertures, wherein each set may differ from other sets in number and/or size of apertures in the set.

Particular embodiments may have the sleeve and second body comprised of respective portions of a locking mechanism for stabilizing a position of the sleeve relative to the second body in order to set a predetermined rate of solute-containing solution dispersal.

The teachings of the present invention also provide methods for dispensing a controlled amount of solute-containing solution. An exemplary method entails providing a floating device having a floatation cap, a first body in releasable communication with the floatation cap, at least a second body in retractable communication with the first body, and a sleeve in sliding communication with the second body, whereby said second body and said sleeve are at least partially retractable within the first body. Particular aspects of the methods provided herein may include separating the floatation cap from the first body in order to dispose a halogen containing solid within the solute-dispending unit comprising at least a first body, and replacing the floatation cap onto the first body. In one embodiment, in order to control the dispersion of solute-containing solution, a user may position the sleeve at a predetermined position relative to the second body for controlling flow of liquid into and out of a space defined at least in part by the first and/or second bodies and then subsequently places the floatation device onto a body of liquid, such as a body of water. The methods taught herein may also comprise the steps of retracting and/or extending components of the solute-dispending unit and/or of determining a dispersion rate for dispersing solute-containing solution into the body of liquid and utilizing the determined rate in positioning said sleeve relative to said second body, as will be detailed below.

The solute-containing solid utilized according to the teachings of the present invention is typically comprised of a halogen such as at least one of fluorine, chlorine, bromine and iodine.

This invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

FIG. 4 is a frontal view of a locking configuration accordance with an exemplary embodiment of the invention;

FIG. 4a is a side cut away view of the locking configuration in FIG. 4;

FIG. 7 depicts a side cut away view of a portion of sleeve and second body portion;

FIG. 7a is a cross-sectional view of an exemplary position securing mechanism;

DETAILED DESCRIPTION OF THE PREFERRED EMBODIMENTS

While the specification describes particular embodiments of the present invention, those of ordinary skill can devise variations of the present invention without departing from the inventive concept and scope of the present invention.

Figure 1:
FIG. 1 is a perspective view of one embodiment according to the teachings of the invention.

Referring more particularly to the Figures, FIG. 1 illustrates a perspective view of an exemplary embodiment of a floating device 2 for dispersing a solute-containing solution according to the teachings of the present invention. Generally, the floating device 2 is comprised of at least two general components, which themselves may be further comprised of additional components. Exemplary component floatation cap 4 and solute-dispensing unit 6 are depicted in FIG. 1. In this embodiment, the solute-dispensing unit 6 is depicted in a retracted state.

Floatation cap 4 is exemplarily depicted having an animal design. While floatation cap 4 may have any desired shape or configuration, typically aesthetically pleasing designs are preferable. In particular, a turtle, duck or other animal or organism may be utilized. For instance, if the apparatus provided by the teachings of the present invention is to be utilized in a pool, floatation cap 4 may be provided having any aesthetically pleasing form, including, but not limited to the animal designs previously mentioned. Plant designs, including flowers, as well as other designs are also contemplated. Of course, floatation cap 4 must be configured so as to provide the proper buoyancy and orientation when disposed in a body of liquid, as known in the art.

Figure 1A:
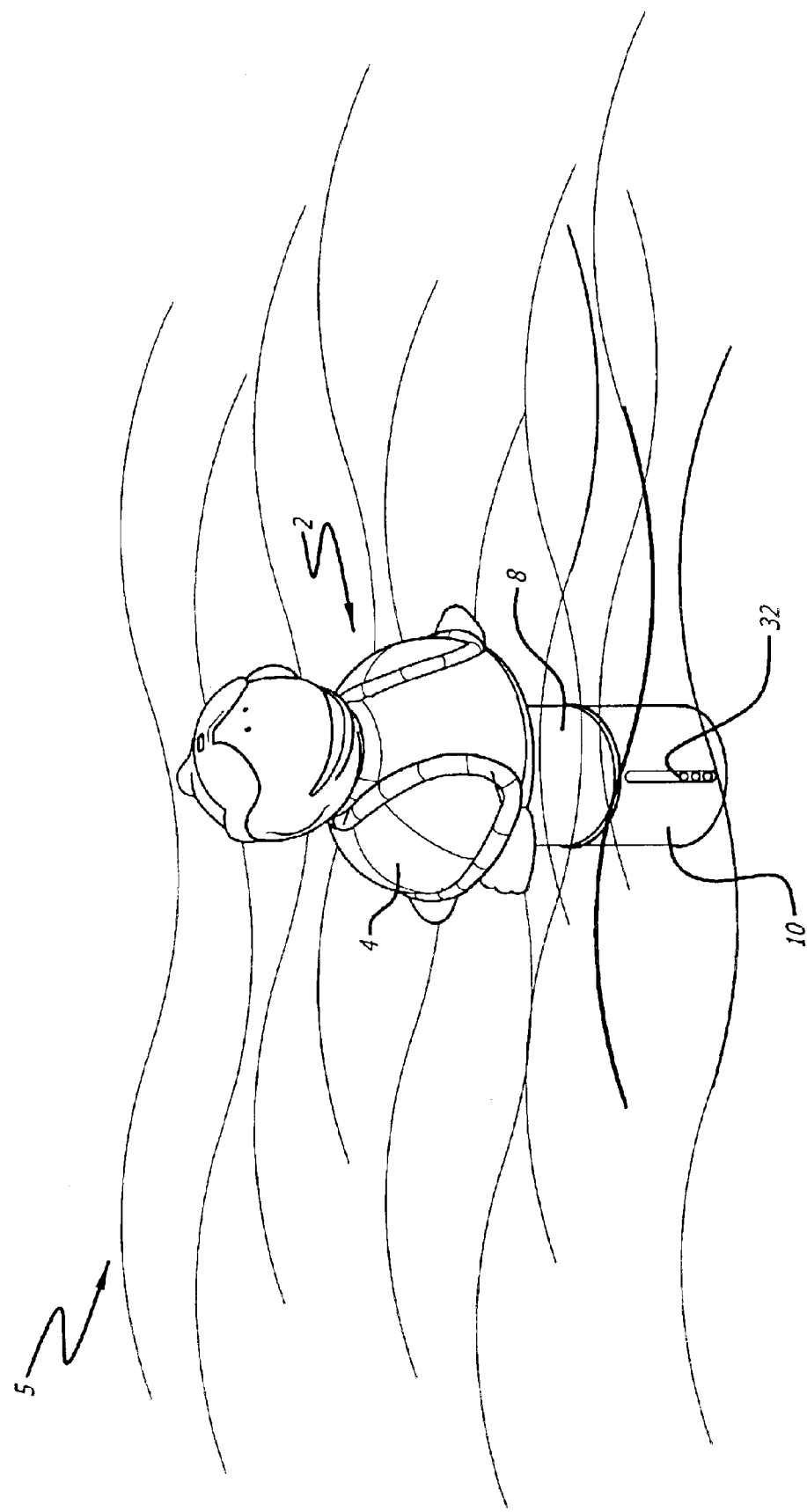
FIG. 1a is a perspective view of one embodiment of the invention disposed in a body of liquid.

Turning to FIG. 1*a*, this embodiment of the invention is shown disposed into a body of liquid 5, typically, but not limited to water, in one state of use, namely having solute-dispensing unit 6 in the protracted state. As shown in FIG. 1*a*, a selected plurality of apertures 32 are displayed to the body of liquid 5 in order to provide a particular rate of dispersion of solute-containing solution that is formed within solute-dispensing unit 6, as further described below.

Figure 2:
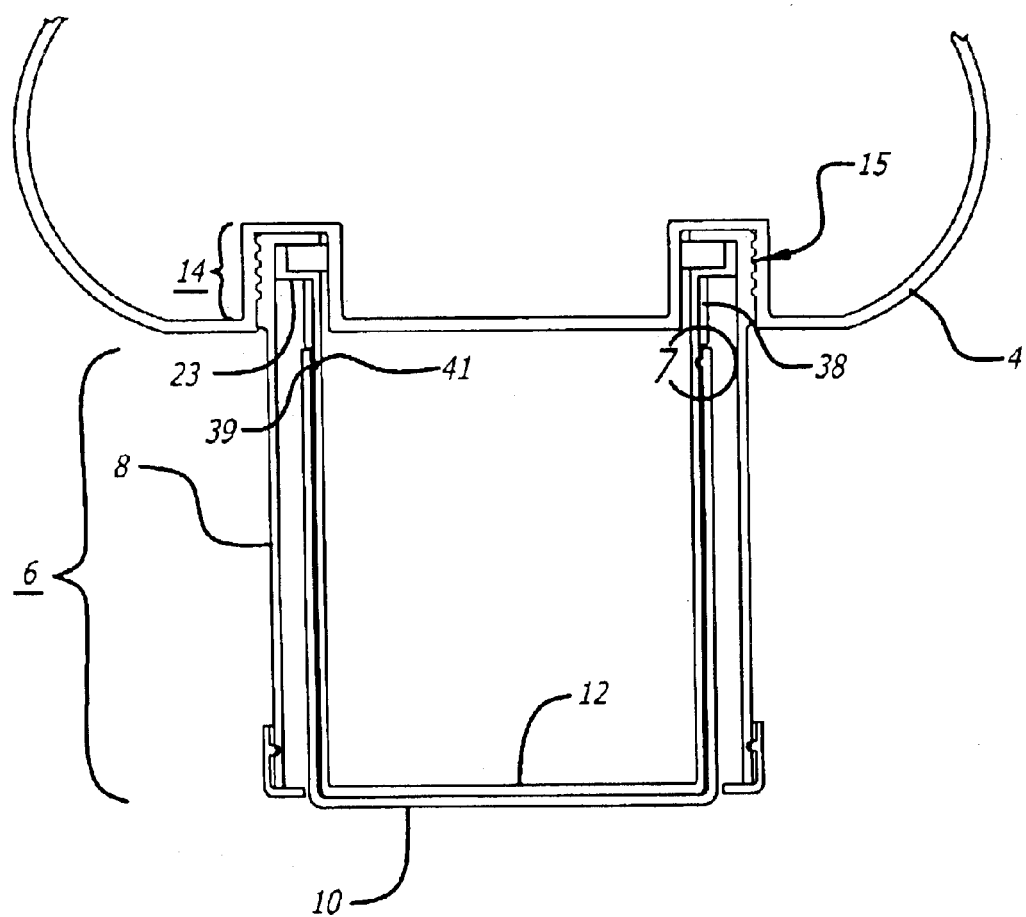
FIG. 2 is a cut away view of a particular embodiment of the invention in a retracted state.

FIG. 2 is a cut away of a particular embodiment in accordance with the teachings of the present invention. Floatation cap 4 is provided with exemplary releasable communication portion 14, by which a first body 8 of solute dispensing unit 6 is in releasable communication with floatation cap 4. Releasable communication portion 14 may be provided by any convenient configuration by which at least a portion of floatation cap 4 releasably communicates with at least a portion of first body 8. In an exemplary embodiment, as shown in FIG. 2, floatation cap 4 and first body 8 are provided with complementary threaded portions 15. Other configurations that provide releasable communication include, but are not limited to friction fits, snap-together lip and recess configurations, snap fits, recess and locking lug and other releasable communication configurations.

As shown in FIG. 2, first body depends from floatation cap 4. Also shown in FIG. 2 are second body 12 and sleeve 10. These components can be at least partially retractable within first body 8. In this particular view, solute-dispensing unit 6 is in a retracted state. Second body 12 is provided with retention means so as to maintain retractable communication with first body 8. As exemplarily depicted, second body 12 may have a flanged portion 23 as a retaining means for maintain retractable communication with first body 8, particularly when solute-dispensing unit 6 in the protracted state, as discussed below and shown in FIG. 3. In addition, second body 12 may also be provided with at least one protuberance 38, and preferable a plurality of protuberances, provided such that when solute-dispensing unit 6 is in the protracted state, the least one protuberance 38 provides a means for securing second body potion 12 in the protracted position relative to first body 8. This may be provided by at least one slightly raised portion 31 disposed upon at least one protuberance 38, that when positioned below retaining ring 36, releasably secures second body 12 and sleeve 10 in the protracted state as shown in FIG. 3.

In one embodiment, sleeve 10 may be provided with a raised portion 39 that fits into a corresponding recess 41 in second body 12, or vice versa. Recess 41 may proceed at least partially around second body 12 such that sleeve 10, having raised portion 39 may be moved and differentially positioned in relation to second body 12, according to a user. Various position securing mechanisms and methods for setting and retaining sleeve 10 in a desired position in relation to second body 12 may be employed. An exemplary position-locking mechanism 7 utilizes a ratchet-type configuration, as detailed below.

Figure 3:
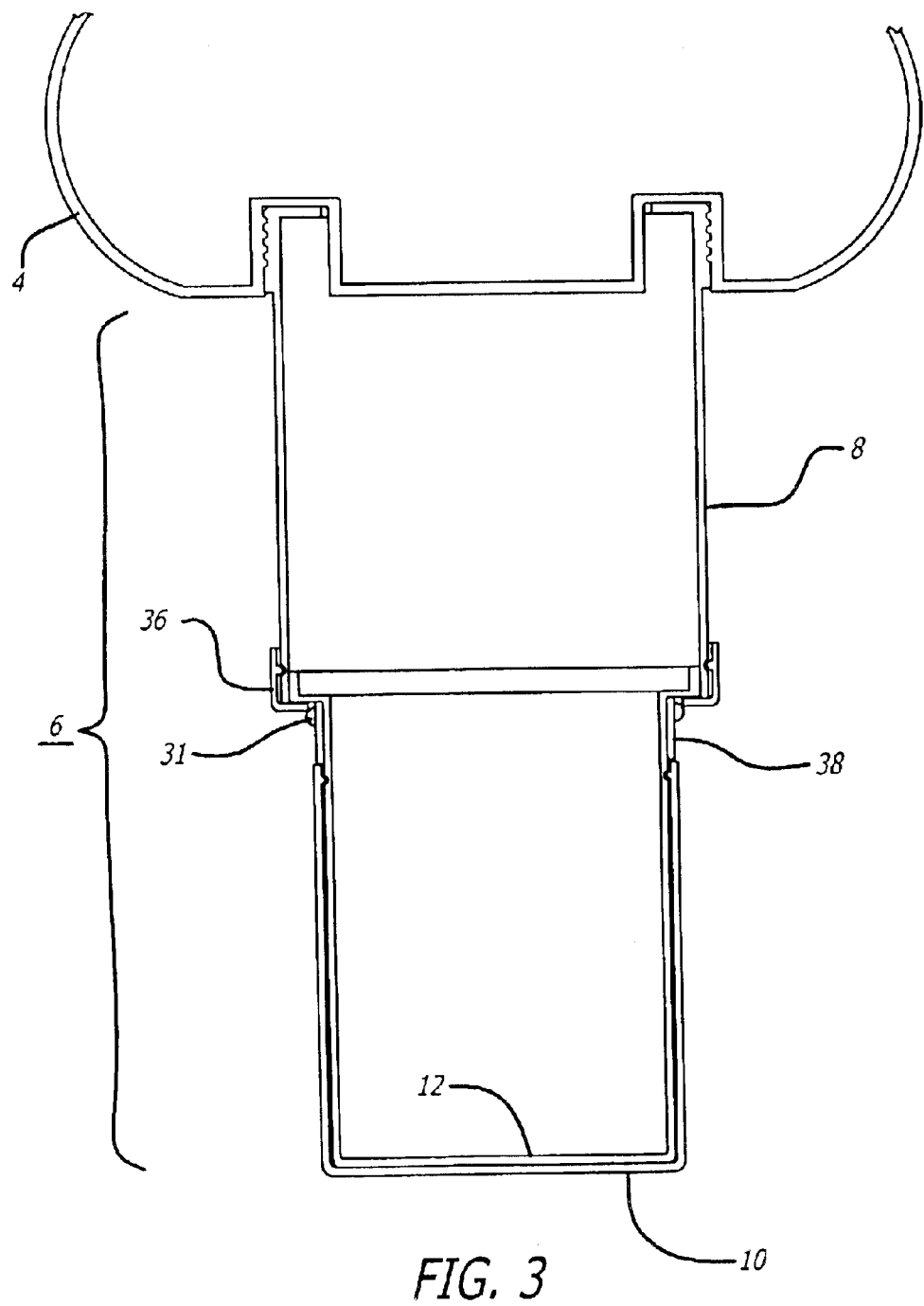
FIG. 3 is a cut away view of the embodiment in a protracted state.

FIG. 3 depicts a cut away view of the embodiment wherein solute dispensing unit 6 is in a protracted state, the at least one slightly raised portion 31 disposed upon at least one protuberance 38 that, when positioned below retaining ring 36, stabilizes this protracted state.

FIG. 4 is a frontal view of a locking configuration on first body 8 in accordance with an exemplary embodiment of the invention. Threads 22 are depicted in this example for providing releasable communication of first body 8 with floating cap 4, as previously discussed. Additionally, at least one aperture 16 is provided in first body 8 as a passageway by which a liquid may pass into and/or out of the space where the solute-containing solution is created, defined by at least first body 8, which is then dispersed into the body of liquid being treated. Also, at least one component of one releasable lock 18, may be provided as part of first body 8 in order to prevent unintentional separation of first body 8 from floating cap 4. Also, exemplary lock 18 may also provide a degree of "child-proofing" the floating device of the present invention, so that access to halogen containing salt disposed within the device, for example, is restricted. A side view of the locking configuration in this exemplary embodiment is shown in FIG. 4*a*. Here, lock 18 is comprised of tab 19, having a bump 20 disposed thereon. In one example, when first body 8 is in releasable configuration from floating cap 4 (screwed together), bump 20 is aligned with a corresponding recess in floating cap 4 and locks into place therein. In this embodiment, in order to remove (unscrew) floating cap 4 from first body 8 having exemplary lock 18, lock 18 is disengaged from the corresponding recess in floating cap 4 by depressing tab 19. This allows for subsequent separation of first body 8 from floatation cap 4.

Figures 5, 6:
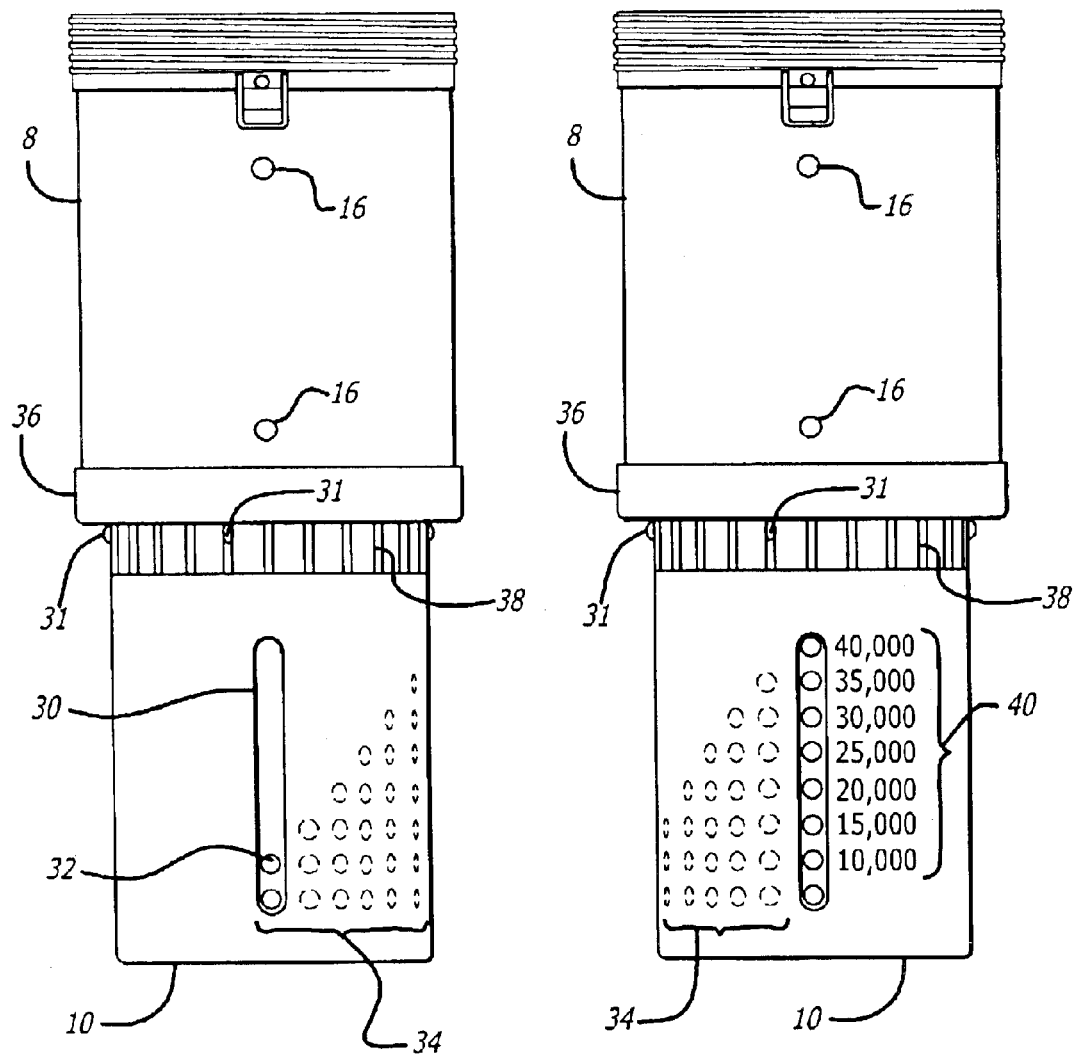
FIG. 5 depicts an exemplary configuration of the invention in protracted state having an apertured sleeve in particular alignment with an apertured second body portion.
FIG. 6 shows the exemplary configuration of FIG. 5 with apertured sleeve in a different position.

FIGS. 5 and 6 depict an exemplary embodiment of the present invention in the protracted state and having sleeve 10, having at least one aperture, in particular alignment with second body 12. Sleeve 10 is provided with at least one aperture 30. Useful apertures may be of any shape or size that provides desired solute solution dispersion rates and do not allow a solid solute containing composition disposed within solute-dispensing unit 6 from falling out. Aperture 30 is alignable with at least one and/or a selected plurality of apertures 32 comprising a series of apertures 34 provided by second body 12, and arranged such that the at least one and/or a selected plurality of apertures 32 are provided so that a particular dispersion rate of solute-containing solution is dispersed when at least one and/or a selected plurality of apertures 32 of the series of apertures 34 is displayed to a body of liquid while other apertures are obscured. Such series of apertures 34 may be a graduated series of columns and/or rows of apertures wherein each column and/or row differs in aperture number and/or size. Indicia 40 may be disposed upon sleeve 12 in order to help a user determine the particular number of apertures to expose to a body of liquid, that is, to select a pre-determined rate of dispersal of the solute-containing solution that is formed within the floating device of the present invention as a result of the combination of liquid conducted into and out of solute-dispensing unit 6. Once contact is thus made, the resultant solute-containing solution is then dispersed out through the apertures and into the body of liquid at the predetermined rate. As shown in FIG. 6, sleeve 10 having aperture 30 is depicted at a position in relation to second body 12 for treating 40,000 gallons of liquid with a solute-containing solution.

FIGS. 7 and 7a are detailed close up views of exemplary position-locking mechanism 7 that may be utilized in order to stably position sleeve 10 in a pre-determined position in relation to second body 12, in order to preserve a selected solute-containing solution dispersion rate. FIG. 7 is a close up cut away view of sleeve 10 having exemplary raised portion 39 fitting into corresponding recess 41 in second body 12. In the cross sectional view of FIG. 7A, exemplary position-locking mechanism 7 is comprised of a ratchet-type configuration having second body disposed teeth 28 and at least one corresponding engageable portion 26 for securing the relative position of sleeve 10 to second body 12. Other position-locking mechanisms/configurations may also be utilized in order to stably position sleeve 10 in a predetermined position in relation to second body 12, such as, but not limited to, friction fits, corresponding bumps and recesses and other configurations, as known in the art.

Figure 8:
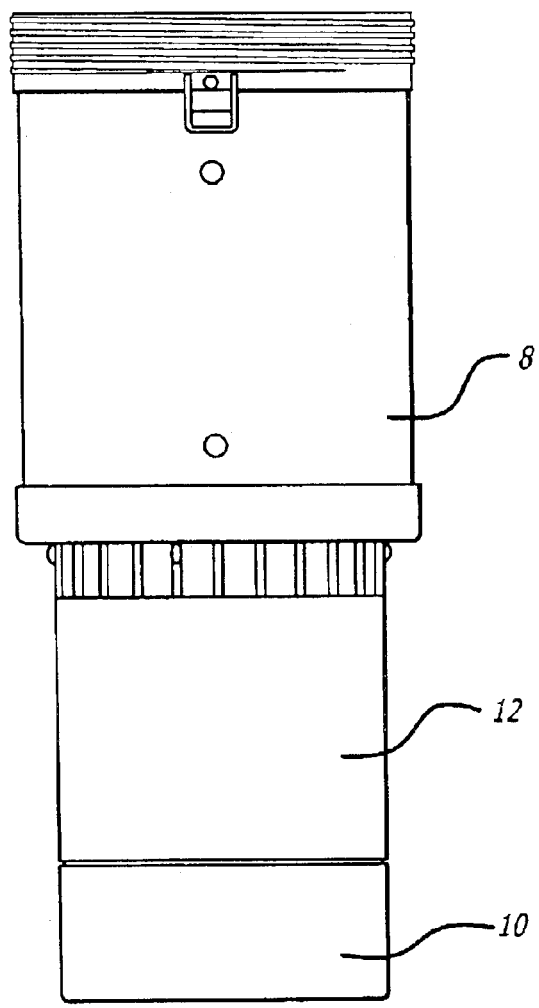
FIG. 8 is a side view of another embodiment according to the teachings of the present invention.
Figure 8A:
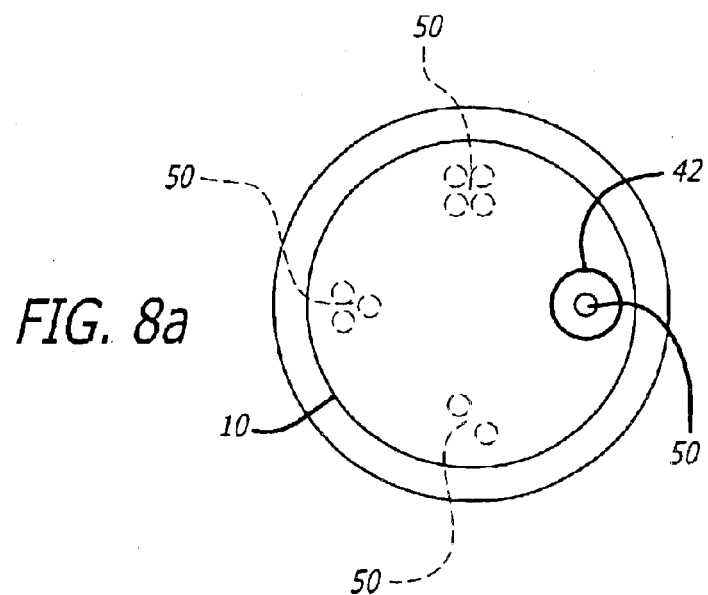
FIG. 8a is a bottom view of the embodiment depicted in FIG. 8.

Another exemplary embodiment of the present invention is depicted in FIG. 8. Here, instead of having the various apertures on the sides of second body 12 and sleeve 10, the apertures are positioned at the bottom of the respective components. Turning to FIG. 8a, a bottom view of the exemplary solute-dispensing unit 6 of FIG. 8, is shown. In this embodiment, sleeve 10 is provided with at least one aperture 42, which may be aligned with a selected aperture or various groups of apertures 50 provided at the bottom of second body 12, by rotation of sleeve 10 to a selected position in order to disperse solute containing solution at the desired rate (the more apertures displayed to the body of liquid, the more solute-containing solution dispersed). Here again, various position-locking mechanisms may be utilized, in accordance with the teachings of the present invention and as known in the art, in order to secure sleeve 10 at a selected position.

While a plurality of apertures has been depicted on various particular components of the floating device for dispersing a solute-containing solution, the apertures as disclose herein may be provided by other components and vise versa. Additionally, while the embodiment discussed herein has a first body 8 into which the second body 12 and sleeve 10 may at least partially retract, additional configurations are also contemplated. For example, the floating device for dispersing a solute-containing solution may be comprised of additional retractable body segments which may or may not have apertures. Furthermore these additional segments may or may not have additional sleeves such that the solute containing solution may be disposed at a particular desired depth and/or differing rates of solute dispersion may be provided at various depths, as taught by the present invention. Furthermore, while particular embodiments disclosed herein depict sleeve 10 in rotatable communication with second body 12, sleeve 10 can be provided in any convenient postionable configuration that provides selectable dispersion rates according to the teachings of the present invention.

The foregoing description of the preferred embodiments of the invention has been presented for the purposes of illustration and description. It is not intended to be exhaustive or to limit the invention to the precise form disclosed. Many modifications and variations are possible in light of the teachings of the present invention.

We claim:

1. A floating device for dispersing a solute-containing solution comprising:

a floatation cap;
a first body in releasable communication with the floatation cap;
a second body capable of receiving a solute-containing solid, in slidable telescoping retractable communication with said first body; and
a sleeve in sliding communication with the second body, whereby said second body and said sleeve are at least partially retractable within said first body.

2. The floating device of claim 1 wherein said first body has at least one aperture.

3. The floating device of claim 1 wherein said second body is further comprised of at least one aperture.

4. The floating device of claim 3 wherein a plurality of apertures by at least one of said bodies are provided in an arrangement that provides a particular dispersion rate of the solute-containing solution when a pre-determined portion of the plurality of apertures is displayed to a body of liquid.

5. The floating device of claim 1 wherein the sleeve is further comprised of at least one aperture.

6. The floating device of claim 5 wherein the sleeve and second body are further comprised of respective portions of a position securing mechanism for stabilizing a position of the sleeve relative to the second body.

7. The floating device of claim 1 wherein said second body has a flanged portion at one end.

8. The floating device of claim 7 wherein said flanged portion is further comprised of at least one protuberance or at least one protuberance having at least one raised portion for locking said second body in an protracted position.

9. The floating device of claim 4 wherein the arrangement of the plurality of apertures is a series of apertures which facilitate the dispersion of the solute-containing solution according to a selected positioning of the sleeve relative to the second body.

10. The floating device of claim 9 wherein the series of apertures is a graduated arrangement of columned series of apertures comprised of a plurality of columns or columns and rows of apertures.

11. The floating device of claim 1 further comprising a locking ring at an end of the first body for retaining said second body in retractable communication with the first body.

12. The floating device of claim 4 wherein the plurality of apertures are provided in a columned arrangement, each column having a predetermined number of apertures.

13. A method for dispensing a controlled amount of solute-containing solution comprising:

providing a floating apparatus having a floatation cap, a solute dispersion unit having a first body in releasable communication with the floatation cap, a second body capable of receiving a solute-containing solid in sliding telescoping communication with said first body and a sleeve in positionable communication with the second body, whereby said second body and said sleeve are at least partially retractable in relation to the first body;
separating the floatation cap from the first body;
disposing a solute-containing solid within at least one chamber defined by the first or second body;
replacing the floatation cap onto the first body;
positioning the sleeve in a predetermined position relative to the second body for controlling flow of liquid into and out of a space defined at least in part by the first and second bodies; and
disposing the floatation device onto a body of liquid.

14. The method of claim 13 wherein the solute-containing solid of the disposing step is comprised of a halogen.

15. The method of claim 14 wherein said halogen is at least one of fluorine, chlorine, bromine and iodine.

16. The method of claim 13 wherein the second body of the providing step is further comprised of at least one aperture.

17. The method of claim 16 wherein the sleeve of the providing step is further comprised of at least one aperture.

18. The method of claim 17 wherein the at least one aperture of the sleeve is configured such that when aligned in a predetermined position relative to the second body, determines the amount of solute-containing solution dispersed into the body of liquid.

19. The method of claim 18 wherein the configured of the at least one aperture of the second body or the sleeve is part of a plurality of apertures, wherein the plurality of apertures are provided in a graduated arrangement such that the positioning step displays a particular aperture configuration to the body of liquid.

20. The method of claim 13 further comprising the step of determining a dispersion rate for dispersing solute containing solution into the body of liquid and utilizing the determined rate for positioning said sleeve relative to said second body.

21. The method of claim 13 further comprising the step of extending or retracting at least one component of the solute dispersion unit.

22. An apparatus for dispersing a solute containing solution, comprising;
    a floatation portion capable of floating in a body of liquid;
    a first portion of an at least two-portion telescoping assembly, in communication with the floatation portion;
    a second portion of said at least two portion telescoping assembly in slidable engagement with said first portion; and
    a sleeve having at least one opening that is positionable relative to at least one portion of said at least two portion telescoping assembly.

23. An apparatus for dispersing a solute containing solution, comprising;
    a floatation element; and
    a telescoping assembly having at least two portions, slidably engaged, in communication with said floatation element, the assembly having an opening in a wall of the telescoping assembly, and said telescoping assembly constructed for containing a solute for dispersion in a liquid surrounding the assembly.

24. The apparatus of claim 23, wherein at least one of said telescoping assembly's telescoping portions is provided with an opening.

25. The apparatus of claim 23, wherein said telescoping assembly includes a portion having an element for controlling dispersion of said solute containing solution.

26. The apparatus of claim 25, wherein said element is a sleeve in sliding communication with a portion of said telescoping assembly.

27. The apparatus of claim 23, wherein said telescoping assembly defines in part a volume capable of holding a halogen containing solid.

28. The apparatus of claim 26, wherein said telescoping assembly has at least one opening and said sleeve has at least one opening for selective positioning relative to the opening in the telescoping assembly.

29. The apparatus of claim 25, wherein said portion having an element for controlling dispersion of said solute containing solution is slidable relative to other portions of said telescoping assembly.

30. The apparatus of claim 25, wherein said element for controlling dispersion of said solute containing solution is constructed such that its position relative to said portion of the telescoping assembly provides control of a rate at which said solute containing solution is dispensed.

31. An apparatus, comprising;
    a floatation portion;
    a telescoping assembly portion including a plurality of slidably engaged portions adjacent and in communication with said floatation portion, wherein said floatation and telescoping assembly portions define a volume into which a solute may be disposed, and a sleeve having at least one opening relative to a portion of said telescoping assembly having at least one opening, wherein a dispersion rate of a solute containing solution is provided by selective positioning of said sleeve.

32. The apparatus of claim 31, wherein said portion of said telescoping assembly having at least one opening is in movable communication with said sleeve, said portion being also in slidable retractable communication within said telescoping assembly.

33. An apparatus for dispersing a solute containing solution, comprising;
    a floatation element; and
    a telescoping assembly in communication with said floatation element, wherein said telescoping assembly has a plurality of portions, wherein a distal most portion has a least one opening and is in communication with a control element, said control element having at least one opening, wherein a solute containing solution dispersal rate is selected by relative positioning of said control element to said distal most telescoping portion of said telescoping assembly.

34. An apparatus for dispersing a halogen-containing solution into a body of liquid, comprising:
    a floating portion;
    a telescoping segmented assembly having a plurality of slidably engaged segments in communication with said floating portion, wherein said telescoping segmented assembly defines a space, said space for containing a halogen-containing solid for providing a solute containing solution, wherein one of said plurality of segments is provided with a solute-containing solution dispersion element, wherein said solute-containing solution dispersion element regulates a dispersion rate of said solute-containing solution into said body of liquid in which said apparatus is placed.

35. The apparatus of claim 34, wherein said one of said plurality of segments has at least one opening and said solute-containing solution dispersion element has at least one opening, wherein the relative positioning of said respective openings to one another determine a dispersion rate of said solute-containing solution into said body of liquid.

* * * * *